US012029446B2

United States Patent
Duffy et al.

(10) Patent No.: US 12,029,446 B2
(45) Date of Patent: Jul. 9, 2024

(54) SURGICAL SITE SUPPORT ARTICLE

(71) Applicant: Medtronic Vascular, Inc., Santa Rosa, CA (US)

(72) Inventors: Niall F. Duffy, Tuam (IE); Yves Bayon, Lyons (FR)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 527 days.

(21) Appl. No.: 17/205,471

(22) Filed: Mar. 18, 2021

(65) Prior Publication Data

US 2021/0290265 A1   Sep. 23, 2021

Related U.S. Application Data

(60) Provisional application No. 62/991,351, filed on Mar. 18, 2020.

(51) Int. Cl.
| | | |
|---|---|---|
| *A61F 2/95* | (2013.01) | |
| *A61B 17/34* | (2006.01) | |
| *A61B 17/00* | (2006.01) | |
| *A61L 31/00* | (2006.01) | |

(52) U.S. Cl.
CPC ...... *A61B 17/3423* (2013.01); *A61B 2017/00004* (2013.01); *A61B 2017/00889* (2013.01); *A61B 2017/3425* (2013.01); *A61B 2017/3429* (2013.01); *A61L 31/005* (2013.01)

(58) Field of Classification Search
CPC . A61F 2/95; A61F 2/958; A61B 17/34; A61B 17/3423; A61B 2017/00004; A61B 2017/1205; A61B 2017/3429; A61B 2017/3425

See application file for complete search history.

(56) References Cited

U.S. PATENT DOCUMENTS

| | | | |
|---|---|---|---|
| 5,569,273 A | 10/1996 | Titone et al. | |
| 9,968,714 B2 | 5/2018 | Fujimoto et al. | |
| 10,034,736 B2 | 7/2018 | Blackburn et al. | |
| 2006/0142798 A1 | 6/2006 | Holman et al. | |
| 2008/0027483 A1* | 1/2008 | Cartledge | .......... A61B 17/0644 606/100 |
| 2019/0247050 A1* | 8/2019 | Goldsmith | ................ A61F 2/82 |

FOREIGN PATENT DOCUMENTS

CA         2733300 C      6/2014

OTHER PUBLICATIONS

Wong et al., "Technical considerations to avoid pitfalls during transapical aortic valve implantation", The Journal of Thoracic and Cardiovascular Surgery, Jul. 2010, pp. 196-202.

\* cited by examiner

*Primary Examiner* — Vi X Nguyen
(74) *Attorney, Agent, or Firm* — Medler Ferro Woodhouse & Mills PLLC (57) ABSTRACT

In some examples, a medical device includes a substrate defining a central port configured to provide surgical access to a surgical site opposite the substrate during a surgical procedure; and a plurality of reinforcement features disposed around the central port, wherein each reinforcement feature of the plurality of reinforcement features is configured to receive a suture, and wherein the plurality of reinforcement features are positioned to cause the substrate to tighten around the central port in response to tension being applied to ends of at least one suture connecting two or more reinforcement features.

22 Claims, 6 Drawing Sheets

SURGICAL SITE SUPPORT ARTICLE

CROSS-REFERENCE TO RELATED APPLICATIONS

This application claims the benefit under 35 U.S.C. § 119(e) of the filing date of U.S. Provisional Application No. 62/991,351, filed Mar. 18, 2020, the contents of which are incorporated by reference herein in their entirety.

TECHNICAL FIELD

This disclosure relates to medical devices.

BACKGROUND

During some surgical procedures, a surgeon may stitch a "purse string" of a suture around a circumference of an incision. The purse string allows the surgeon to close the incision after the surgical procedure is complete by pulling on the ends of the suture, causing the purse-string stitch to collapse toward the incision at its center. The ends of the suture may then be tightly tied, sealing the incision.

SUMMARY

The disclosure describes a surgical article configured to provide support and strength to a surgical site, such as the apical region of the heart, which is used to gain trans-apical access to a ventricle and/or atrium of the heart during some catheter-based surgical cases such as aortic and/or mitral valve-replacement. In some examples, a medical device includes a substrate defining a central port configured to provide surgical access to a surgical site opposite the substrate during a surgical procedure; and a plurality of reinforcement features disposed around the central port, wherein each reinforcement feature of the plurality of reinforcement features is configured to receive a suture, and wherein the plurality of reinforcement features are positioned to cause the substrate to tighten around the central port in response to tension being applied to ends of at least one suture connecting two or more reinforcement features.

In some examples, a method of performing a surgical operation includes applying a substrate to a biological tissue at a surgical site of a patient; weaving a suture through a plurality of reinforcement features surrounding a central port of the substrate; inserting a surgical instrument through the central port into an incision in the tissue; pulling on ends of the suture to tighten the tissue around the surgical instrument; performing a surgical operation; removing the surgical instrument from the central port of the substrate; and pulling on the ends of the suture to close the incision in the tissue.

The details of one or more examples are set forth in the accompanying drawings and the description below. Other features, objects, and advantages will be apparent from the description and drawings, and from the claims.

DETAILED DESCRIPTION

This disclosure describes example medical devices, systems, and techniques for performing a surgical procedure at a surgical site within a patient, such as a region of the heart, and more specifically, the apex of the heart. For example, the surgeon may cut an incision into the biological tissue of the heart and insert one or more surgical tools into the incision to perform a surgical operation. After the surgery is complete, the surgeon may withdraw the surgical tool(s) from the incision and sew the incision closed by weaving a suture through the biological tissue immediately surrounding the incision.

In some examples in accordance with this disclosure, a medical article includes a layer of fabric, tissue, or other substrate, configured to be attached to a patient's biological tissue at a surgical site within the patient. The medical article may reinforce the patient's biological tissue to which the article is attached. For example, during a surgical procedure, a surgeon may thread a suture through one or more selected locations of the article. The article may help redistribute a force or pressure applied between the suture and the patient's biological tissue. In some examples, the article may include a plurality of reinforcement features. The reinforcement features may both guide the surgeon as to where to insert the suture, as well as further reinforce the article and, ultimately, the underlying tissue.

In some examples, the reinforcement features may be arranged so as to define a "purse string" stitch when a suture is threaded through the respective features. For example, after a surgeon threads a suture through a circular arrangement of reinforcement features, the surgeon may easily collapse the circular arrangement, and the underlying tissue, around an incision substantially centered within the circular arrangement by applying force or tension to the ends of the suture. In this way, the surgeon may seal a surgical incision while and/or after performing a surgical procedure through the incision.

In some examples, the plurality of reinforcement features may include a networked pattern of reinforcement features, wherein individual features are physically connected by a larger reinforcement structure attached to or embedded within the substrate. The reinforcement structure may further reinforce an underlying tissue of the patient by distributing forces or tensions from a suture across the larger pattern, while still allowing for natural movement of the underlying tissue.

Figure 1:
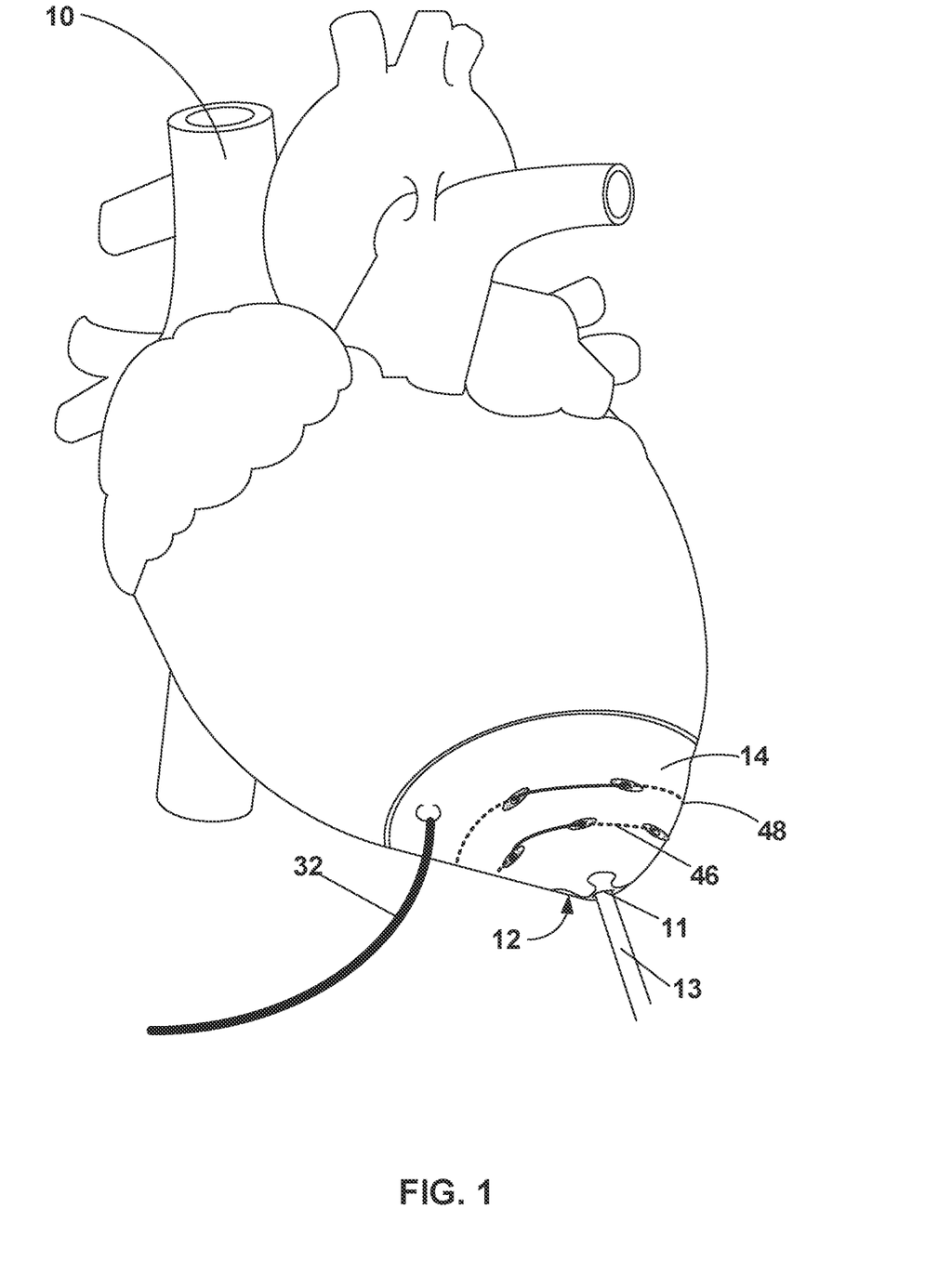
FIG. 1 is a conceptual diagram depicting a first example surgical article applied to an apical region of a heart, in accordance with techniques of this disclosure.

FIG. 1 is a conceptual diagram depicting a first example surgical article 14 applied to an apical region 12 of a heart 10 of a patient, in accordance with techniques of this disclosure. As described further below, surgical article 14 may provide added structural support to biological tissue during a surgical procedure, reducing a likelihood and/or severity of unwanted perforations in the tissue.

For example, during a surgical procedure, a surgeon may insert a surgical tool 13 into an incision 11 in heart 10. Surgical tool 13 may include any instrument used during a surgical procedure. For example, surgical tool 13 may include a medical catheter having an inner lumen. In some examples, the inner lumen may be configured to receive an additional surgical instrument to pass the additional surgical instrument through incision 11, such as to implant a stent, a replacement valve, or another medical device. In some examples, a medical catheter may be configured to withdraw tissue through incision 11, such as a thrombus located within the heart 10. In other examples, surgical tool 13 may include a scope or other viewing instrument for use during an exploratory or laparoscopic procedure. In some examples, a surgeon may insert more than one surgical tool 13 through incision 11 simultaneously.

After performing a surgical procedure via incision 11, the surgeon may withdraw the one or more surgical tools 13 from incision 11 and sew incision 11 closed. For example, the surgeon may weave or sew a length of suture 46 into the biological tissue immediately surrounding incision 11. For example, the surgeon may weave a length of the suture back and forth directly overtop of incision 11 in order to close the incision. Additionally or alternatively, as shown in FIG. 1, the surgeon may sew an approximately circular ring of suture 46 around the circumference of incision 11. This style or pattern may be referred to as a "purse string" stitch, in that the surgeon may seal the incision 11 by pulling on the ends of suture 46, causing the circular ring to collapse around incision 11, similar to the opening of a draw-string bag. In some examples, the surgeon may additionally sew a second purse string of a suture 48 around the circumference of the first purse string 46. By collapsing the second purse string 48, the surgeon may further reinforce the sealing of incision 11 and provide redundancy should the initial purse string 46 fail.

In some examples, the contact between either or both sutures 46, 48 and the biological tissue into which they are sewn may impart a relatively large amount of force or pressure to the biological tissue, particularly during and after the surgeon collapses the purse string stitch(es) around incision 11.

In some examples in accordance with this disclosure, before performing the surgical procedure, the surgeon may attach surgical article 14 to the patient's biological tissue. Surgical article 14 may help to protect and/or reinforce the patient's biological tissue by receiving and redistributing the force or pressure from sutures 46, 48. For example, surgical article 14 may include a plurality of embedded reinforcement features configured to guide the insertion of surgical sutures 46, 48 into the biological tissue, as well as reinforce the biological tissue immediately surrounding each suture insertion point.

In some examples, as shown in FIG. 1, a surgical procedure may include the use of a pacemaker to maintain heart rhythm during and/or after the surgical procedure. In some of these examples, a surgeon may affix a fixation element of a pacemaker's pacing lead 32 into the fabric, tissue, or other substrate of surgical article 14 as a fixation mechanism to restrain pacing lead 32. In this way, pacing lead 32 may remain physically coupled to (e.g., remain in electrically conductive contact with) the biological tissue of heart 10. Pacing lead 32 may remain attached to surgical article 14 for a period of time, such as 3-5 days, after the surgical procedure, in case the patient is in need of cardiac pacing.

Figure 2:
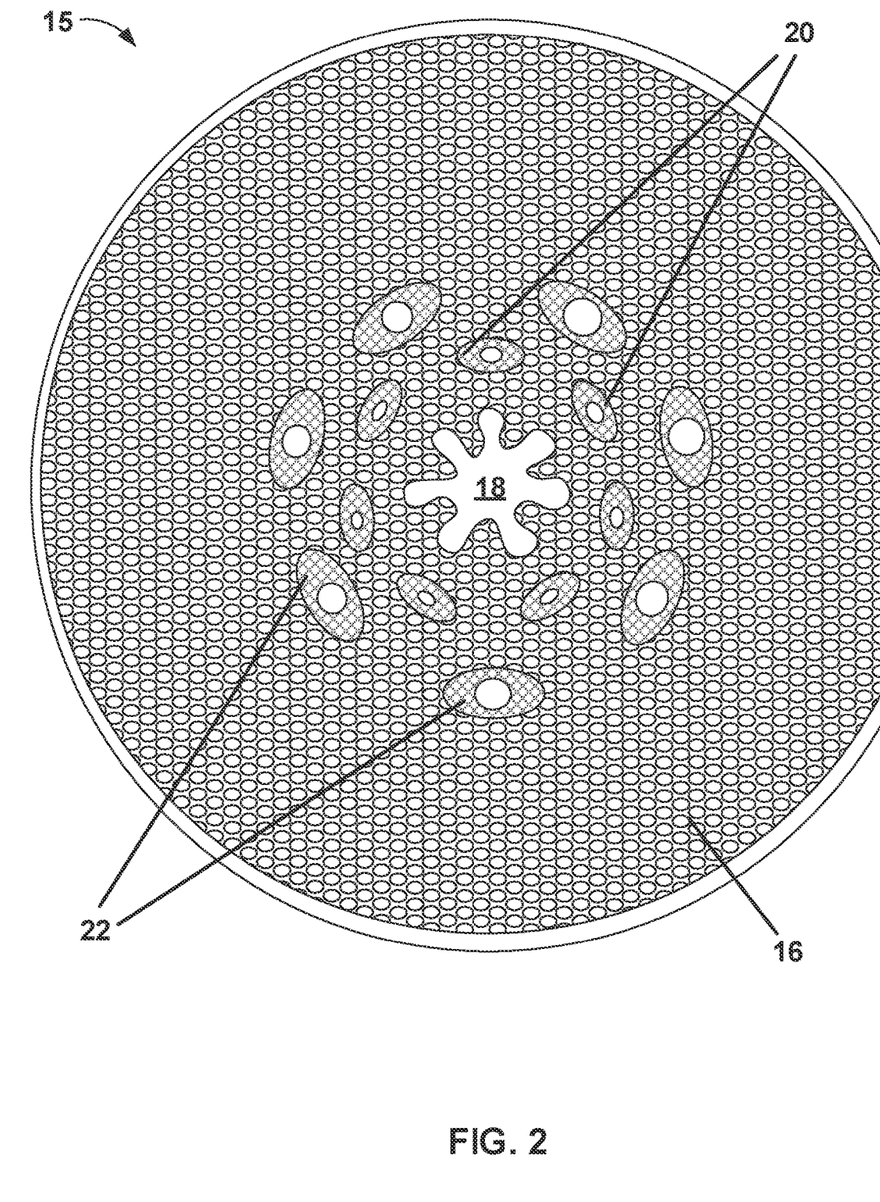
FIG. 2 is a plan view of an example surgical article, in accordance with techniques of this disclosure.

FIG. 2 is a plan view of an example of a surgical article 15 in accordance with this disclosure. Surgical article 15 may include an example of surgical article 14 of FIG. 1. Surgical article 15 includes a substrate 16, a central port 18, and a plurality of suture reinforcement features 20, 22. Substrate 16 may include virtually any substantially thin, flat (e.g., planar) material, configured to align with a biological tissue at a surgical site of a patient. In the example of FIG. 2, substrate 16 includes a substantially circular shape, for example, defining a substantially circular perimeter. In other examples, the outer perimeter of substrate 16 may take the form of any geometric shape as appropriate to fit the respective surgical site. In some examples, the outer perimeter of substrate 16 may be configured to be cut or trimmed from an initial "standard" geometric shape into a different geometric shape customized to fit the surgical site of a particular surgical procedure. For example, the substrate may define a thickness that decreases near the outer perimeter, allowing the edges of the substrate to be easily cut or trimmed.

In some examples, such as the example depicted in FIG. 2, substrate 16 may include a fabric mesh. A fabric mesh may include any biocompatible material configured to provide mechanical support to tissue, e.g., heart 10 during and/or after a surgical procedure. In some examples, substrate 16 may be composed of biocompatible woven threads or filaments. For example, the biocompatible material may be a naturally occurring material, a naturally derived material, or a synthetic material. In some examples, but not all examples, the threads or filaments may be temporary or bioresorbable, so as to dissolve or resorb into the body of the patient over a period of time after a surgical procedure. In some examples, the fabric material may include a combination of permanent and temporary filaments. For example, the threads may be manufactured from polyglycolic acid, polypropylene, polyethylene terephthalate (PET), or polytetrafluoroethylene (PTFE), polylactic acid (e.g., poly-L-lactic acid), or the like. In some examples, the threads or filaments may include a relatively lubricious material, such as a hydrogel or lubricious polymer, in order to reduce friction between surgical article 15 and any biological tissue to which article 15 is not attached while article 15 is located at the surgical site within the patient. For example, the lubricious filaments may include polyvinylpyrrolidone (PVP), polyurethanes, polyacrylic acid, polyethylene oxide, a polysaccharide, or a hydrophobic polymer such as PTFE or silicone.

In some examples, as shown in FIG. 2, the threads or filaments of substrate 16 may be relatively loosely woven, such that the fabric features a repetitive mesh pattern of holes or openings, making the fabric relatively pliable or stretchable as compared to a more densely woven fabric, such as denim.

In other examples, substrate 16 include a material other than a woven threads or filaments. For example, substrate 16 may include a harvested biological tissue, for example, a porcine or bovine pericardium tissue. The pliability or stretchability of substrate 16 may allow for the natural systolic motion of the heart while the substrate 16 is attached to the biological tissue of the heart.

Substrate 16 defines central port 18. Central port 18 includes a hole or opening through which a surgeon may insert one or more tools to perform a surgical procedure at the surgical site. As shown in FIG. 2, in some examples, central port 18 may include a substantially irregular shape, allowing the substrate defining the perimeter of central port 18 to easily expand and collapse as needed throughout the surgical procedure. For instance, central port 18 may define a corrugated or wavy perimeter having one or more curved, convex, and/or concave portions that provide slack to enable stretching of the material surrounding central port 18. In other examples, central port 18 may include a circular, elliptical, or polygonal shape.

In some examples in accordance with this disclosure, surgical article 15 includes a plurality of reinforcement features 20, 22, either affixed to, or embedded within, substrate 16. Each of reinforcement features 20, 22, includes a unit of material defining an opening (or "eyelet") configured to receive a length of a surgical suture, such that the suture may be stitched into the biological tissue of the patient while surgical article 15 is applied at the surgical site. In some examples, but not all examples, either or both of reinforcement features 20, 22, and/or substrate 16 may be formed of a fabric mesh material. Reinforcement features 20, 22 may include a bioresorbable material, as described with respect to substrate 16 above, or in some examples, a different bioresorbable material.

Reinforcement features 20, 22 are configured to fortify surgical article 15 in a region surrounding the suture. For example, because a surgical suture is relatively thin (e.g., has a relatively small cross-sectional area), any force applied to the surgical suture may translate into a substantially large pressure at a location where the suture contacts surgical article 15 and/or a biological tissue of the patient. Accordingly, in some examples, reinforcement features 20, 22 may be made from a material that is stronger than the material of substrate 16. For example, reinforcement features 20, 22 may be formed from a material having a higher density than the material of substrate 16, such as a fabric material that is more-densely woven, more-densely braided, or more-densely stitched than a fabric material of substrate 16. Additionally or alternatively, reinforcement features 20, 22 may be formed from a material having a higher tensile strength than the material of substrate 16, such as a fabric material including filaments having a larger thread diameter or a chemically distinct thread material defining a higher tensile strength. In other examples, reinforcement features 20, 22 may be composed of practically any biologically-compatible material, such as polyester, plastic, biological tissue, or other material.

Reinforcement features 20, 22, may be arranged in a particular configuration with respect to substrate 16. In some examples, as depicted in FIG. 2, reinforcement features may include a first plurality of "inner" reinforcement features 20 arranged in a circular shape immediately surrounding central port 18. In this circular arrangement, a surgeon is able to create a "purse string" stitch by weaving a surgical suture 46 (FIG. 1) through the respective openings of consecutive inner reinforcement members 20. The purse-string stitch allows the surgeon to collapse the circular arrangement of inner reinforcement features 20 toward their common center, by applying tension to (e.g., pulling on) the ends of the stitched suture 46. In doing so, the surgeon simultaneously collapses the biological tissue to which the surgical article 15 is affixed, inward towards a surgical incision centered within the central port 18. The purse-string stitch provides at least two functions. First, the surgeon may use the stitch to tighten the patient's tissue around a surgical tool that has been inserted into the incision through central port 18 during a surgical procedure, reducing the likelihood of unwanted material or other contamination either entering or exiting through the incision. Second, after the surgeon has completed the surgical procedure and has removed the surgical tool from the incision through central port 18, the surgeon may tightly collapse the purse-string stitch and secure the ends of the suture in order to close and seal the incision at the center. In the example depicted in FIG. 2, surgical article 15 includes seven inner reinforcement features 20, although surgical article 15 may include any number of inner reinforcement features greater than two.

In some examples, surgical article 15 additionally includes a second plurality of "outer" reinforcement features 22 arranged in a circular shape surrounding the first plurality of inner reinforcement features 20. The outer reinforcement features 22 are configured to receive a second surgical suture 48 (FIG. 1), allowing a surgeon to implement a second purse-string stitch in addition to the first. A second purse-string stitch may close and seal the incision even more tightly than the first purse-string stitch alone, and provides redundancy in case the first purse-string stich should fail. In the example depicted in FIG. 2, surgical article 15 includes seven outer reinforcement features 22, although surgical article 15 may include any number of outer reinforcement features greater than two.

Figure 3:
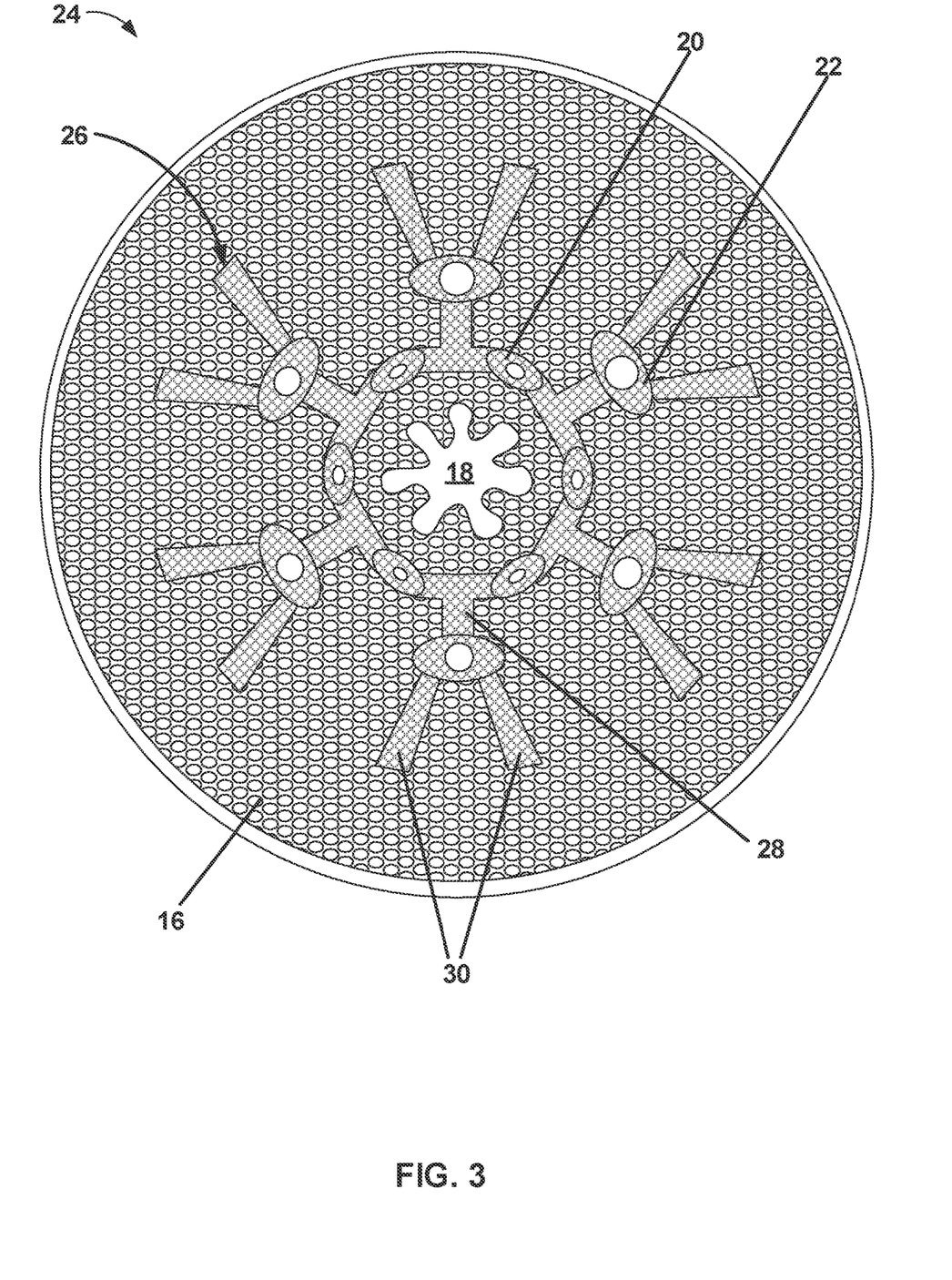
FIG. 3 is a plan view of a second example surgical article including a web-like support structure, in accordance with techniques of this disclosure.

FIG. 3 is a plan view of a second example surgical article 24 including a web-like support structure, in accordance with techniques of this disclosure. Surgical article 24 may be an example of surgical article 14 of FIG. 1. Similar to surgical article 15 of FIG. 2, surgical article 24 includes a substrate 16, a central port 18, and a plurality of reinforcement features 20, 22. For example, surgical article 24 may include six inner reinforcement features 20 and six outer reinforcement structures 22. In other examples, article 24 may include any number of reinforcement features, such as four inner reinforcement features 20 and six outer reinforcement features 22.

In the example depicted in FIG. 3, surgical article 24 additionally includes a web-like support structure 26 (alternatively, "support web 26") coupled to the substrate. In some examples, support web 26 may be configured to further reduce (e.g., redistribute) a force or strain applied to a suture stitched through the reinforcement features, while still allowing for the natural diastole and systole movement of the apical tissue (e.g., motion due to the beating of the heart). For example, while substrate 16 and reinforcement features 20, 22 may locally redistribute pressure in the region immediately surrounding each suture entry point, by connecting individual reinforcement features 20, 22, support web 26 may help to further redistribute the pressure across a larger region of substrate 16.

Support web 26 may include a fabric or other substrate structure connecting the plurality of inner reinforcement features 20 to the plurality of outer reinforcement features 22. In some examples of surgical article 24, support web 26 may be composed of the same or substantially the same material as reinforcement features 20, 22. In some examples, substrate 16 may include a bioresorbable material and support web 26 may include a substantially non-bioresorbable material. In other examples, any or all components of surgical article 24, including substrate 16, reinforcement features 20, 22, and/or support web 26, may be composed of a bioresorbable material.

In the non-limiting example shown in FIG. 3, support web 26 includes a support ring 28 connecting each of the plurality of inner reinforcement features 20, as well as a pair of support legs 30 extending radially outward from each outer reinforcement feature 22. For example, as shown in FIG. 3, support ring 28 includes a plurality of "T"-shaped reinforcement structures, each "T"-shape configured to connect two inner reinforcement features 20 to one outer reinforcement feature 22 and to each other.

Support legs 30 include a pair of linear reinforcement features extending radially outward (as defined by central port 18) from each outer reinforcement feature 22. It is to be understood that the example support web 26 depicted in FIG. 3, including support ring 28 and support legs 30, is not intended to be limiting. Other configurations of support web 26 may achieve similar techniques, for example, to interconnect different numbers of inner reinforcement features 20 and outer reinforcement features 22, respectively.

In some examples, the surgeon may further redistribute forces across surgical article 24 through various patterns of suture(s). For example, a surgeon may stitch an additional suture extending radially from at least one inner reinforcement feature 20 to at least one outer reinforcement feature 22, such that, when the surgeon collapses the inner purse string stitch, the outer purse string stitch may partially contract as well. In some examples, the surgeon may stitch an additional "X" shape of suture overtop various points along the existing purse-string stitch(es), so as to further redistribute a force from the purse-string stitch into the region of substrate 16 immediately surrounding the "X" shapes.

Figure 4:
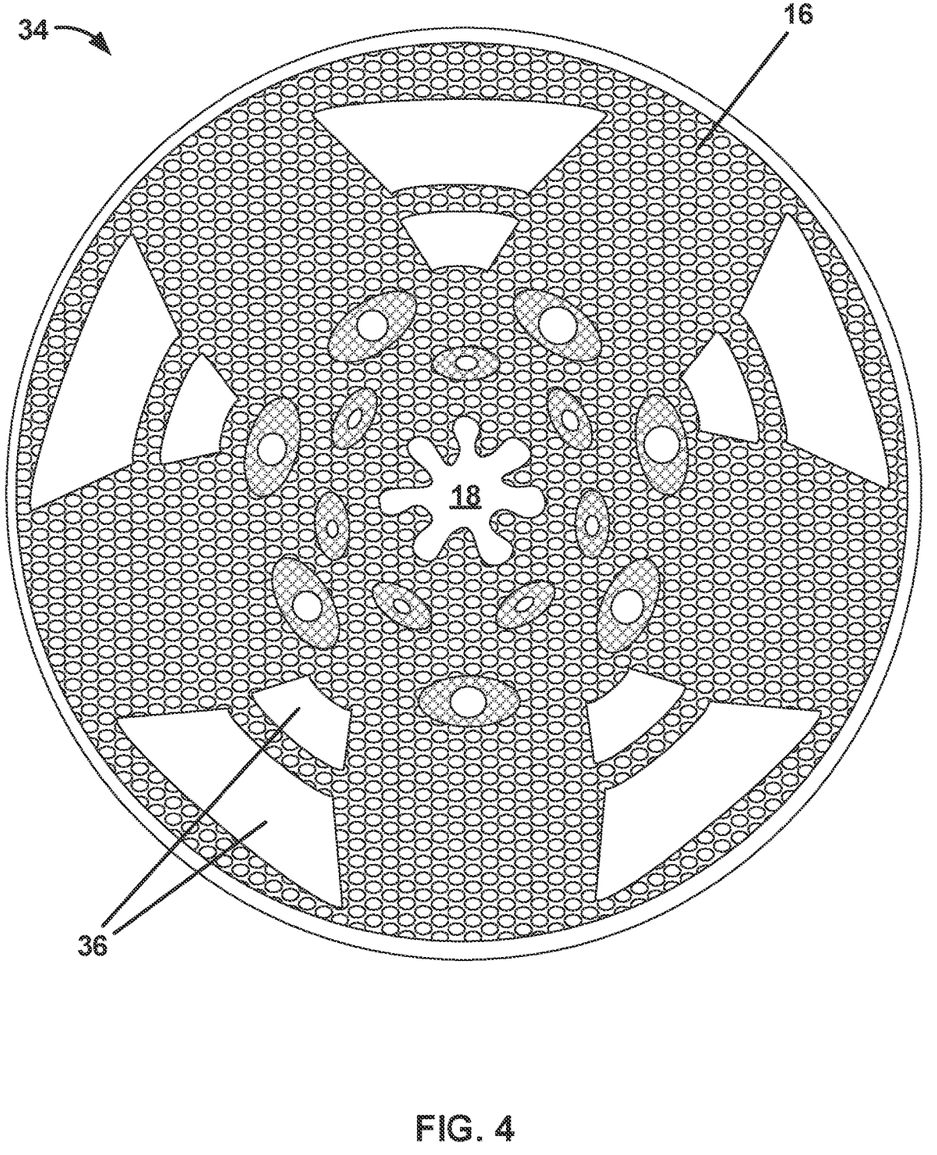
FIG. 4 is a perspective view of a third example surgical article defining a web-like support structure, in accordance with techniques of this disclosure.

FIG. 4 is a perspective view of a third example surgical article 34, in accordance with techniques of this disclosure. Surgical article 34 may be an example of surgical article 14 of FIG. 1. Similar to surgical article 24 of FIG. 3, surgical article 34 of FIG. 4 is configured to define a web-like structure to redistribute a radial load applied to each reinforcement feature when the surgeon collapses a purse-string stitch of suture (not shown in FIG. 4). However, rather than defining a web-like structure 28 through additional material coupled to the base substrate 16 as in FIG. 3, surgical article 34 of FIG. 4 defines a web-like structure via a plurality of windows 36 cut or removed from substrate 16, such that the substrate 16 itself defines the web structure. In some examples of surgical article 34, the thickness and/or density (as defined above) of substrate 16 may increase radially outward from central port 18 such that the overall structural integrity of surgical article 34 remains approximately consistent as a function of the radius of the substrate 16.

Figure 5:
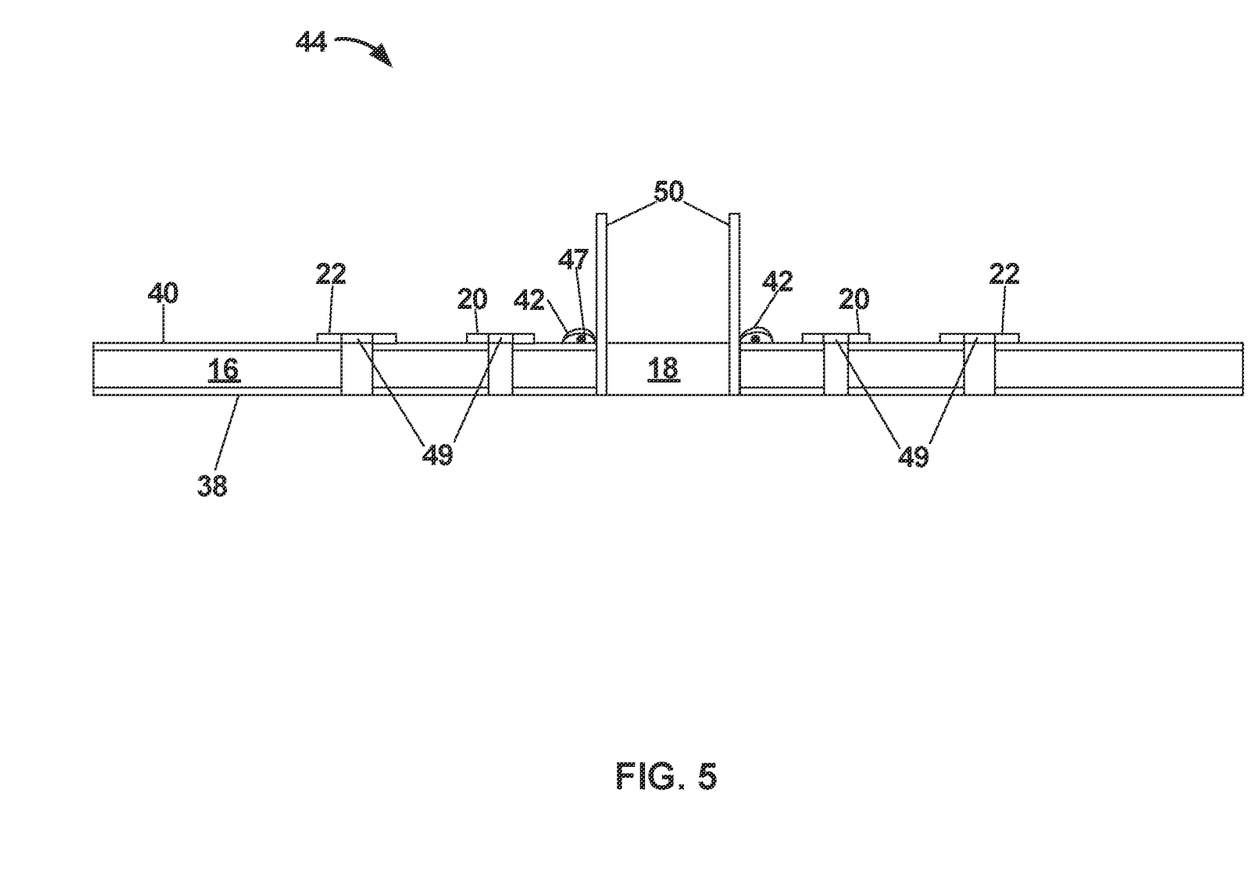
FIG. 5 is a cross-sectional side view of an example surgical article, in accordance with techniques of this disclosure.

FIG. 5 is a cross-sectional side view of an example surgical article 44, in accordance with techniques of this disclosure. Surgical article 44 may be an example of surgical article 14 of FIG. 1. It should be noted that the example of FIG. 5 is included for illustrative purposes only, and has not necessarily been drawn to scale, and any example surgical article 44 may include more, fewer, or different features than those depicted in FIG. 5. Surgical article 44 includes a substrate material 16. Substrate 16 may include practically any material suitable to perform the techniques of this disclosure. In some examples, substrate 16 may include jersey fabric (e.g., the type of material known for having originated in Jersey Island of the English Channel Islands). In other examples, substrate 16 may include a biological tissue, such as a porcine pericardium tissue. In other examples, substrate 16 may include a surgical mesh fabric as described above.

In some examples, substrate 16 and/or other components of surgical article 44 may be composed of bioresorbable materials, e.g., materials designed to break down over a period of time and disperse into the circulatory system, from which it may eventually be naturally evacuated from the body of the patient. For example, substrate 16 may be composed of a bioresorbable poly-L-lactic acid mesh fabric. In some example, substrate 16 may have an approximately planar circular shape. For example, substrate 16 may have a diameter of between about 1 and 2 inches, or between about 2.5 and 5 centimeters.

Surgical article 44 defines central port 18. Central port 18 may include an opening at or near the center of substrate 16, configured to receive one or more surgical instruments or tools 13 (FIG. 1). Central port 18 may include an irregular geometric shape configured to facilitate expansion and contraction of the port. In examples in which central port 18 is approximately circular, central port 18 may define a circumference or width of between about 0.2 and 0.6 inches, or between about 0.5 and 1.5 centimeters.

Surgical article 44 may include a plurality of inner suture reinforcement features 20 and/or a plurality of outer suture reinforcement features 22. Either or both sets of reinforcement features 20, 22 may include approximately circular or oval-shaped eyelets defining a respective central opening 49 configured to receive a surgical suture. For example, inner reinforcement features 20 may be configured to receive a first length of suture 46 (FIG. 1), and outer reinforcement features 22 may be configured to receive a second length of suture 48 (FIG. 1). The suture reinforcement features may be composed of a stronger or more durable material than substrate 16, such that a suture fed through one of the reinforcement features may be less likely to perforate substrate 16.

In some examples, surgical article 44 includes an adhesive coating 38 applied to an underside of substrate 16, configured to attach surgical article 44 to a biological tissue of a patient. Surgical article 44 may additionally or alternatively include an anti-microbial coating 40 configured to sterilize surgical article 44 during and/or after a surgical procedure using surgical article 44. Although anti-microbial coating 40 is depicted in FIG. 5 as being applied to a top side of substrate 16, in other examples, anti-microbial coating 40 may be distributed throughout any or all of substrate 16 and/or reinforcement features 20, 22.

In some examples, surgical article 44 may include a plurality of pre-defined folds (not shown in FIG. 5), either stitched directly into the structure of substrate 16 or formed (e.g., heat-set) into an originally planar material of substrate 16. The pre-defined folds may guide or otherwise facilitate the collapsing of a purse-string stitch to seal an incision when a surgeon pulls on the ends of a suture stitched through reinforcement features 20, 22.

In some examples, additionally or alternatively to reinforcement features 20, 22, surgical article 44 may include a hem stitch 42 surrounding the perimeter of central port 18. Surgical article 44 may include a suture 47 fed between hem stitch 42 and substrate 16. The suture 47 fed underneath hem stitch 42 may additionally form a purse-string stitch, such that a tension applied to the ends of suture 46 may cause the circular hem stitch 42 to collapse toward the center of central port 18, thereby sealing surgical article 44 and/or the proximal biological tissue around a surgical incision 13 (FIG. 1) underneath central port 18.

Suture 47, which may include an example of any suture referenced throughout this disclosure, may include a 4.0 Prolene suture with a size-17 needle. In some examples, a first suture 46 (FIG. 1) may be fed through each of the inner reinforcement features 20, and a second suture 48 (FIG. 1) may be fed through each of outer reinforcement features 22. In some examples, the first and the second sutures may have different colors and/or patterns, so as to assist a surgeon in distinguishing between the two sutures.

In some examples, surgical article 44 may include a detachable seal tube 50 coupled to central port 18. Seal tube 50 may be configured to help maintain homeostasis both before and during a surgical procedure. Seal tube 50 may be configured to be clamped shut for sterility, and may additionally include a flush line (not shown in FIG. 5).

Figure 6:
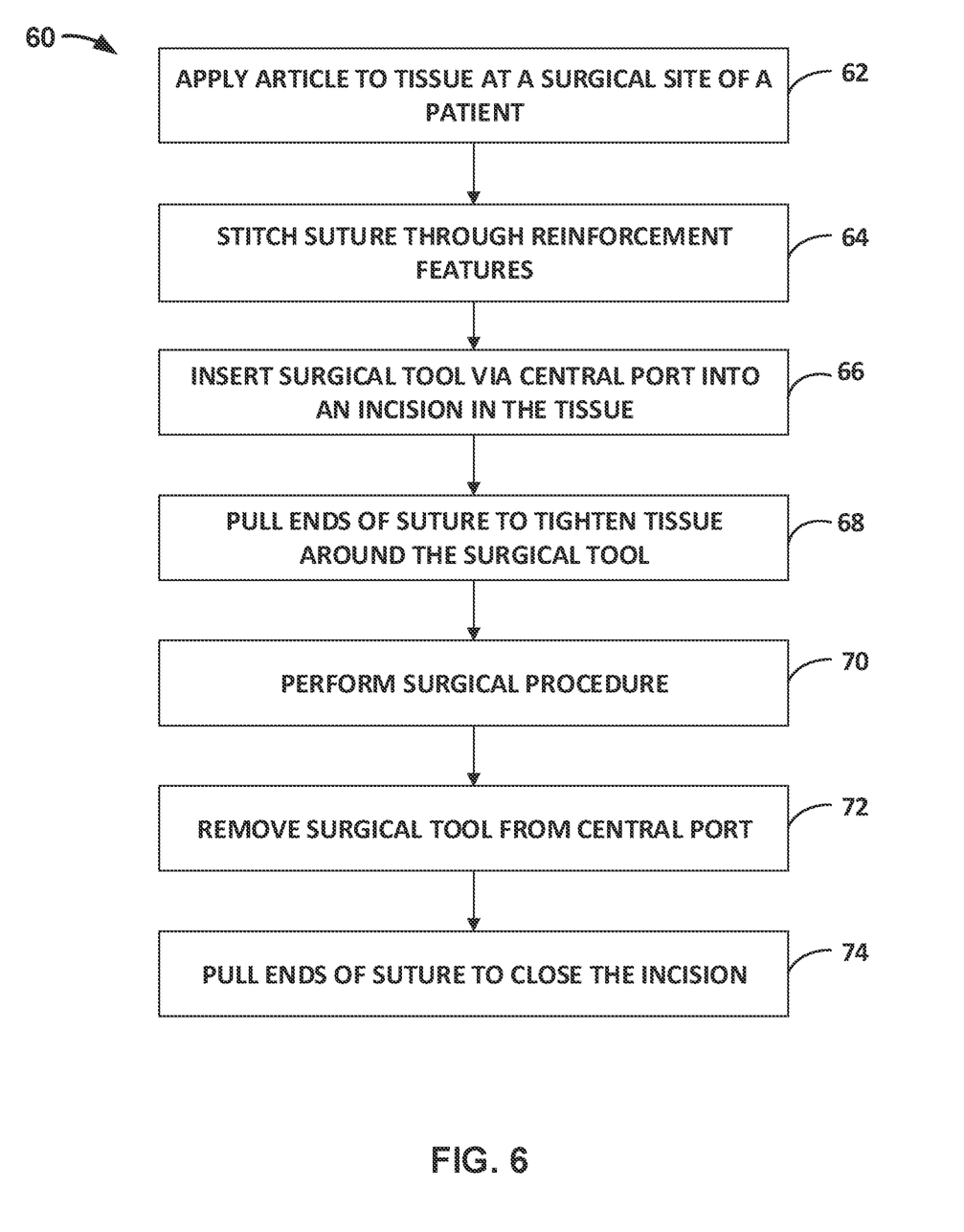
FIG. 6 is a flowchart describing a method of performing a surgical procedure using a surgical article, in accordance with techniques of this disclosure.

FIG. 6 is a flowchart describing a method 60 of performing a surgical procedure using a surgical article, in accordance with techniques of this disclosure. Method 60 is primarily described with respect to a use of surgical article 14 of FIG. 1, however, method 60 may include the use of any surgical article in accordance with the techniques of this disclosure. A surgeon or other qualified operator may apply a surgical article 14 at a tissue site of a patient (62). For example, the surgeon may apply an adhesive coating 38 (FIG. 5) to an underside of the surgical article 14 to a biological tissue of the patient. In some examples, the surgical site may include a pericardium region, such as an apex 12 of a heart 10 of the patient.

Once the surgeon has attached the surgical article 14 to the surgical site, the surgeon may weave a suture 46 through a plurality of reinforcement features 20 attached to the surgical article 14 (64). For example, the surgeon may feed a needle attached to the suture through an eyelet hole 49 (FIG. 5) of each reinforcement feature and down into the biological tissue opposite the surgical article 14, further securing the surgical article to the biological tissue. In some examples, the plurality of reinforcement features may form a circular perimeter surrounding a central port 18 of the surgical article. In some examples, the reinforcement features may include a first plurality of "inner" reinforcement features 20 and a second plurality of "outer" reinforcement features 22, forming a second circular perimeter around the inner reinforcement features 20. The surgeon may weave a second length of suture 48 through the outer plurality 22. The surgeon may cut an incision into the biological tissue via the central port 18, and insert a surgical tool, such as a laparoscopic tool, into the incision (64). Then, by pulling (e.g., applying tension) to the ends of the suture, the surgeon may cause the circular plurality of reinforcement features to move toward central port 18, located at the common center of the circular plurality of reinforcement features (66). By partially collapsing the circular ring of reinforcement features toward their common center, the surgeon may tighten the surgical article 14 and the biological tissue around the surgical tool, protecting the incision from contamination during the surgical procedure. Using the surgical tool, the surgeon may proceed to perform the surgical procedure (70). Once the surgical procedure is complete, the surgeon may withdraw the surgical tool from the incision via the central port 18 (72). Finally, the surgeon may again apply tension to the ends of the suture to further collapse the ring of reinforcement features toward their common center, thereby closing the biological tissue around the incision (74). The surgeon may tie the ends of the suture together to secure the biological tissue around the incision, thereby allowing the incision to naturally heal closed over time. In examples in which the reinforcement features include both an inner plurality and an outer plurality, the surgeon may additionally pull on the ends of the second suture in order to collapse the outer plurality of reinforcement features around the incision, providing redundant security for closing the surgical incision. In some examples, the surgeon may further seal the incision by applying surgical glue to the cinched purse-string stitch.

The following clauses provide some examples of the disclosure.

Clause 1: In some examples, a device includes a substrate defining a central port configured to provide surgical access to a surgical site opposite the substrate during a surgical procedure; and a plurality of reinforcement features disposed around the central port, wherein each reinforcement feature of the plurality of reinforcement features is configured to receive a suture, and wherein the plurality of reinforcement features are positioned to cause the substrate to tighten around the central port in response to tension being applied to ends of at least one suture connecting two or more reinforcement features.

Clause 2: In some examples of the device of clause 1, the plurality of reinforcement features includes a plurality of inner reinforcement features disposed around the central port; and a plurality of outer reinforcement features disposed around the plurality of inner reinforcement features.

Clause 3: In some examples of the device of clause 1 or clause 2, the substrate defines a substantially circular perimeter.

Clause 4: In some examples of the device of clause 2, the plurality of eyelets includes at least four inner reinforcement features and at least six outer reinforcement features.

Clause 5: In some examples of the device of any of clauses 1-4, the central port includes an irregular perimeter configured to facilitate expansion and contraction of the central port.

Clause 6: In some examples of the device of any of clauses 1-5, the substrate includes a first fabric mesh and the reinforcement features each include a second fabric mesh, wherein the second fabric mesh has a higher density than the first fabric mesh.

Clause 7: In some examples of the device of any of clauses 1-6, the substrate or the plurality of reinforcement features include a bioresorbable material.

Clause 8: In some examples of the device of clause 7, the substrate comprises a bioresorbable poly-L-lactic acid mesh.

Clause 9: In some examples of the device of any of clauses 1-8, the device further includes an anti-microbial coating.

Clause 10: In some examples of the device of clause 2, the device includes a support web attached to the substrate, the support web connects the plurality of inner reinforcement features to the plurality of outer reinforcement features, and the support web is configured to leave diastole and systole movement of the apex of the heart substantially unaffected.

Clause 11: In some examples of the device of clause 10, the support web includes a support ring connecting the plurality of inner reinforcement features and the plurality of outer reinforcement features; and a pair of support legs extending radially from each outer reinforcement feature.

Clause 12: In some examples of the device of any of clauses 1-11, the substrate includes a plurality of windows such that the substrate defines a web-like structure.

Clause 13: In some examples of the device of clause 10, the substrate is bioresorbable, and the support web is substantially non-bioresorbable.

Clause 14: In some examples of the device of any of clauses 1-13, the substrate includes an outer circumference configured to be trimmed to custom-fit the surgical site.

Clause 15: In some examples of the device of any of clauses 1-14, the surgical site comprises an apex of a heart of a patient.

Clause 16: In some examples of the device of any of clauses 1-15, the device includes an adhesive coating on the substrate, wherein the adhesive coating is configured to attach the substrate to the surgical site.

Clause 17: In some examples of the device of any of clauses 1-16, the substrate includes a biological tissue.

Clause 18: In some examples of the device of clause 17, the biological tissue includes a pericardium tissue.

Clause 19: In some examples of the device of any of clauses 1-18, the substrate defines a plurality of guide folds configured to guide folding of the substrate in response to the tension being applied to the at least one suture.

Clause 20: In some examples of the device of any of clauses 1-19, the first substrate defines a density that increases radially outward from the central port.

Clause 21: In some examples of the device of clause 2, the at least one suture includes a first suture configured to weave through the inner eyelets and a second suture configured to weave though the outer reinforcement features.

Clause 22: In some examples, a method includes: applying a substrate to a biological tissue at a surgical site of a patient; weaving a suture through a plurality of reinforcement features surrounding a central port of the substrate; inserting a surgical instrument through the central port into an incision in the tissue; pulling on ends of the suture to tighten the tissue around the surgical instrument; performing a surgical operation; removing the surgical instrument from the central port of the substrate; pulling on the ends of the suture to close the incision in the tissue.

Various examples of the disclosure have been described. Any combination of the described systems, operations, or functions is contemplated. These and other examples are within the scope of the following claims.

What is claimed is:

1. A device comprising:
   a substrate comprising a substantially thin, flat material defining a central port extending from an outer surface through an inner surface of the substrate, the central port configured to provide surgical access to a surgical site opposite the inner surface of the substrate during a surgical procedure; and
   a plurality of reinforcement features disposed around the central port, wherein each reinforcement feature of the plurality of reinforcement features is configured to receive a suture, and wherein the plurality of reinforcement features are positioned to cause the substrate to tighten around the central port in response to tension being applied to ends of at least one suture connecting two or more of the reinforcement features.

2. The device of claim 1, wherein the plurality of reinforcement features comprises:
   a plurality of inner reinforcement features disposed around the central port; and
   a plurality of outer reinforcement features disposed around the plurality of inner reinforcement features.

3. The device of claim 2, wherein the plurality of reinforcement features comprises at least four inner reinforcement features and at least six outer reinforcement features.

4. The device of claim 1, wherein the substrate defines a substantially circular perimeter.

5. The device of claim 1, wherein the central port comprises an irregular perimeter configured to facilitate expansion and contraction of the central port.

6. The device of claim 1, wherein the substrate comprises a first fabric mesh and the reinforcement features each comprise a second fabric mesh, wherein the second fabric mesh has a higher density than the first fabric mesh.

7. The device of claim 1, wherein the substrate or the plurality of reinforcement features comprise a bioresorbable material.

8. The device of claim 7, wherein the substrate comprises a bioresorbable poly-L-lactic acid mesh.

9. The device of claim 1, further comprising an anti-microbial coating.

10. The device of claim 1, wherein the substrate comprises a plurality of windows such that the substrate defines a web-like structure.

11. The device of claim 1, wherein the substrate comprises an outer circumference configured to be trimmed to custom-fit the surgical site.

12. The device of claim 1, wherein the surgical site comprises an apex of a heart of a patient.

13. The device of claim 1, further comprising an adhesive coating on the substrate, wherein the adhesive coating is configured to attach the substrate to the surgical site.

14. The device of claim 1, wherein the substrate comprises a biological tissue.

15. The device of claim 14, wherein the biological tissue comprises a pericardium tissue.

16. The device of claim 1, wherein the substrate defines a plurality of guide folds configured to guide folding of the substrate in response to the tension being applied to the at least one suture.

17. The device of claim 1, wherein the first substrate defines a density that increases radially outward from the central port.

18. The device of claim 1, wherein the inner surface of the substrate is configured to contact the surgical site.

19. A device comprising:
    a substrate defining a central port configured to provide surgical access to a surgical site opposite the substrate during a surgical procedure;
    a plurality of reinforcement features disposed around the central port, wherein each reinforcement feature of the plurality of reinforcement features is configured to receive a suture, and wherein the plurality of reinforcement features are positioned to cause the substrate to tighten around the central port in response to tension being applied to ends of at least one suture connecting two or more reinforcement features, wherein the plurality of reinforcement features comprises:
      a plurality of inner reinforcement features disposed around the central port; and
      a plurality of outer reinforcement features disposed around the plurality of inner reinforcement features; and
    a support web attached to the substrate, wherein the support web connects the plurality of inner reinforcement features to the plurality of outer reinforcement features, and wherein the support web is configured to leave diastole and systole movement of the apex of the heart substantially unaffected.

20. The device of claim 19, wherein the support web comprises:
    a support ring connecting the plurality of inner reinforcement features and the plurality of outer reinforcement features; and
    a pair of support legs extending radially from each outer reinforcement feature.

21. The device of claim 19, wherein the substrate is bioresorbable, and wherein the support web is substantially non-bioresorbable.

22. A device comprising:
    a substrate defining a central port configured to provide surgical access to a surgical site opposite the substrate during a surgical procedure;
    a plurality of reinforcement features disposed around the central port, wherein the plurality of reinforcement features comprises:
      a plurality of inner reinforcement features disposed around the central port; and a plurality of outer reinforcement features disposed around the plurality of inner reinforcement features; and a first suture configured to weave through the inner reinforcement features and a second suture configured to weave through the outer reinforcement features, wherein the plurality of reinforcement features are positioned to cause the substrate to tighten around the central port in response to tension being applied to ends of the first suture or the second suture connecting two or more of the reinforcement features.

* * * * *